United States Patent
Nakamura et al.

(10) Patent No.: US 8,096,953 B2
(45) Date of Patent: Jan. 17, 2012

(54) ORGANISM INFORMATION DETECTING APPARATUS

(75) Inventors: Takashi Nakamura, Chiba (JP); Kazuya Maegawa, Chiba (JP); Koichi Moriya, Chiba (JP); Shinichiro Miyahara, Chiba (JP); Kaori Takano, Chiba (JP)

(73) Assignee: Seiko Instruments Inc. (JP)

( * ) Notice: Subject to any disclaimer, the term of this patent is extended or adjusted under 35 U.S.C. 154(b) by 1447 days.

(21) Appl. No.: 10/590,128

(22) PCT Filed: Dec. 16, 2005

(86) PCT No.: PCT/JP2005/023117
§ 371 (c)(1),
(2), (4) Date: Nov. 20, 2006

(87) PCT Pub. No.: WO2006/068037
PCT Pub. Date: Jun. 29, 2006

(65) Prior Publication Data
US 2007/0225586 A1 Sep. 27, 2007

(30) Foreign Application Priority Data
Dec. 20, 2004 (JP) .................... 2004-367975

(51) Int. Cl.
*A61B 5/02* (2006.01)
(52) U.S. Cl. ......... 600/502; 600/481; 600/500; 600/503

(58) Field of Classification Search .......... 600/300, 600/301, 485, 490, 495, 500–507
See application file for complete search history.

(56) References Cited

U.S. PATENT DOCUMENTS

| | | | | |
|---|---|---|---|---|
| 5,697,374 A | * | 12/1997 | Odagiri et al. | 600/500 |
| 6,099,478 A | * | 8/2000 | Aoshima et al. | 600/500 |
| 2004/0116786 A1 | * | 6/2004 | Iijima et al. | 600/301 |
| 2007/0195989 A1 | * | 8/2007 | Tsubata et al. | 382/100 |

* cited by examiner

*Primary Examiner* — Patricia Mallari
(74) *Attorney, Agent, or Firm* — Adams & Wilks (57) ABSTRACT

An organism information detecting apparatus includes a detector that detects organism information of a subject for a predetermined sampling time period, determines a motion state of the subject when the organism information is detected, and outputs an organism signal. A first calculator processes the organism signal to calculate organism information data, the detector determining a reliability degree of the organism information data based on whether the determined motion state of the subject is a previously determined motion state. A second calculator calculates an average value of the amount of variation per time of data obtained by digitizing the organism signal, the average value being data supplementary to the organism information data. The detector determines the motion state of the subject based on whether the supplementary data exceeds a previously determined threshold. A storage device stores the organism information data and the supplementary data such that the organism information data and the supplementary data are associated with one another.

20 Claims, 9 Drawing Sheets

| TASK No. | PREDETERMINED TIME | ACTION | RETURN DATA |
|---|---|---|---|
| 1 | 8.00 | MEASURE PULSE NUMBER | PULSATION NUMBER SUPPLEMENTARY DATA |
| 2 | 9.00 | MEASURE PULSE NUMBER | PULSATION NUMBER SUPPLEMENTARY DATA |
| 3 | 10.00 | MEASURE PULSE NUMBER | PULSATION NUMBER SUPPLEMENTARY DATA |
| 4 | 12.00 | MEASURE PULSE NUMBER | PULSATION NUMBER SUPPLEMENTARY DATA |
| ... | ... | ... | ... |

| DETERMINATION | MOTION STATE | RELIABILITY DEGREE OF ORGANISM INFORMATION DATA | MOTION CONTROL |
|---|---|---|---|
| Vt1 > SUPPLEMENTARY DATA | STATIONARY STATE | HIGH | NORMAL MOTION |
| Vt2 > SUPPLEMENTARY DATA ≧ Vt1 | ORDINARY MOTION STATE | MIDDLE | DISPLAY DISPLAY DATA ONE BEFORE DATA |
| SUPPLEMENTARY DATA ≧ Vt2 | SIGNIFICANT MOTION STATE | LOW | POWER SOURCE DRIVE CIRCUIT POWER SOURCE OFF |

ORGANISM INFORMATION DETECTING APPARATUS

CROSS-REFERENCE TO RELATED APPLICATIONS

This application is a U.S. national stage application of International Application No. PCT/JP2005/023117, filed Dec. 16, 2005, claiming a priority date of Dec. 20, 2004, and published in a non-English language.

TECHNICAL FIELD

The present invention relates to an organism information detecting apparatus for monitoring a state of a subject by detecting organism information of the subject. Further in details, the invention relates to an organism information detecting apparatus for monitoring an organism state of a subject by determining a motion state of the subject in detecting organism information of the subject and using the motion state along with the organism information of the subject.

BACKGROUND ART

In a background art, there is a pulsimeter for irradiating light to the organism tissue including the artery, outputting a pulsation signal of the light based on a change in a light amount of reflecting light or transmitting light in accordance with pulsation of the artery, and measuring a pulsation number during a previously determined measuring time period (for example, 1 minute) based on the pulsation signal. When the pulsation is optically detected in this way, although the subject may preferably be brought into a stationary state, for example, when there is motion of moving the hand or the finger, there poses a problem that noise which is not related to the pulsation is included in the pulsation signal (pulse signal) by being significantly influenced by the physical motion. Particularly, when the pulsation is measured at the arm, it is known that noise is very large even when a detecting person is brought into a stationary state. In order to resolve the problem, there is known a pulsimeter for preventing a deterioration in accuracy of measuring (calculating) the pulsation number by removing a value of an interval of generating a pulsation signal based on an abnormal pulsation signal caused by noise or the like from calculating operation (refer to, for example, Patent Reference 1). Further, as other method, there is known an organism state detecting apparatus for detecting accurate pulsation by separately irradiating fluxes or light having different wavelengths, intensities, light amounts or the like to a subject and analyzing fluxes of reflecting light (refer to, for example, Patent Reference 2).
Patent Reference 1: JP-A-2002-028139
Patent Reference 2: JP-A-2004-261366

DISCLOSURE OF THE INVENTION

Problems that the Invention is to Solve

However, according to technologies shown in Patent References 1 and 2, after finishing the operation, information with regard to noise does not remain and therefore, there poses a problem that even when a data is measured under a preferable condition, and when a data is measured otherwise, the data are dealt with as similar data. For example, when a pulsation number is not necessarily measured always under a preferable condition depending on a state of a subject as in a portable pulsimeter, information of in what state the pulsation number is measured becomes important information in observing a result thereof. In a case in which a subject is in motion to constitute an adverse condition as a measuring condition, when the fact is known, the pulsation can be measured again, however, the fact is not known by technologies shown in Patent References 1 and 2 and therefore, even a measured value having low reliability measured under an adverse condition is obliged to be used as "measured value of subject".

Further, according to the technology shown in Patent Reference 2, fluxes of light having different wavelength, strengths, light amounts or the like need to be used and therefore, the pulsation number cannot be measured by one measuring means to amounts to an increase in extra cost, an increase of a size of the pulsimeter, an increase in power consumption.

The invention has been carried out under such a situation and it is an object thereof to provide an organism information detecting apparatus relating a supplementary data capable of determining a motion state, that is, whether a subject is brought into a stationary state or the like when organism information is detected to organism information data and monitoring an organism state of the subject based on the data.

Further, at this occasion, it is an object thereof to provide supplementary data without additionally needing other organism information detecting means.

Means for Solving the Problems

In order to resolve the above-described problem, the invention is constituted by an organism information detecting apparatus which is an organism information detecting apparatus for detecting organism information of a subject, the organism information detecting apparatus including organism information detecting means for detecting the organism information of the subject by being brought into contact with the subject for a previously determined sampling time period and outputting an organism signal, organism information data calculating means for calculating an organism information data by processing the organism signal, supplementary data calculating means for calculating an average value of a variation amount per time of a data constituted by digitizing the organism signal as a supplementary data of the organism information data, and data storing means for relating the organism information data and the supplementary data to be stored.

Further, the invention is constituted by the organism information detecting apparatus, further including motion state determining means for determining a motion state of the subject when the organism information is detected based on whether the supplementary data exceeds a previously determined threshold.

Further, the invention is constituted by the organism information detecting apparatus, further including reliability degree determining means for determining a reliability degree of the organism information data related to the supplementary data based on whether the motion state determined by the motion state determining means is a previously determined motion state.

Further, the invention is constituted by an organism information processing server which is an organism information processing server for communicating with a distal end of the organism information detecting apparatus, the organism information processing server including communicating means for receiving the organism information data and the supplementary data from the organism information detecting apparatus, data storing means for relating the organism information data and the supplementary data to be stored, motion state determining means for determining a motion state of the subject when the organism information is detected based on whether the supplementary data exceeds a previously determined threshold, and reliability degree determining means for determining a reliability degree of the organism information data related to the supplementary data based on whether the motion state determined by the motion state determining means is a previously determined motion state.

Further, the invention is constituted by an organism information detecting system including the organism information detecting apparatus and the organism information processing server.

Further, the invention is constituted by an organism information processing method for achieving a function provided to the organism information detecting apparatus.

Further, the invention is constituted by an organism information processing method for achieving a function provided to the organism information processing server.

Further, the invention is constituted by an organism information processing method for achieving a function provided to the organism information processing system.

Further, the invention is constituted by a method which is a motion state determining method for determining a motion state in detecting the organism information of the subject executed by the organism information processing apparatus, the motion state determining method comprising a step of acquiring a data constituted by digitizing an organism signal during a previously determined sampling time period outputted by the organism information detecting means, a step of calculating an average value of a variation amount per time of the data, and a step of determining the motion state of the subject when the organism information is detected based on whether the average value of the variation amount exceeds a previously determined threshold.

Further, the invention is a computer readable record medium recorded with a program for making a computer realize a function of determining a motion state of a subject by using a digital data of an organism signal outputted by organism information detecting means which is a computer readable record medium recorded with a program for making the computer realize a function of making the computer read the digital data, a function of calculating an average value of a variation amount per time of the digital data, and a function of determining the motion state of the subject when the organism information is detected based on whether the average value of the variation amount exceeds a previously determined threshold.

BEST MODE FOR CARRYING OUT THE INVENTION

First Embodiment

An explanation will be given of an organism information detecting apparatus according to a first embodiment of the invention in reference to the drawings as follows.

Figure 1:
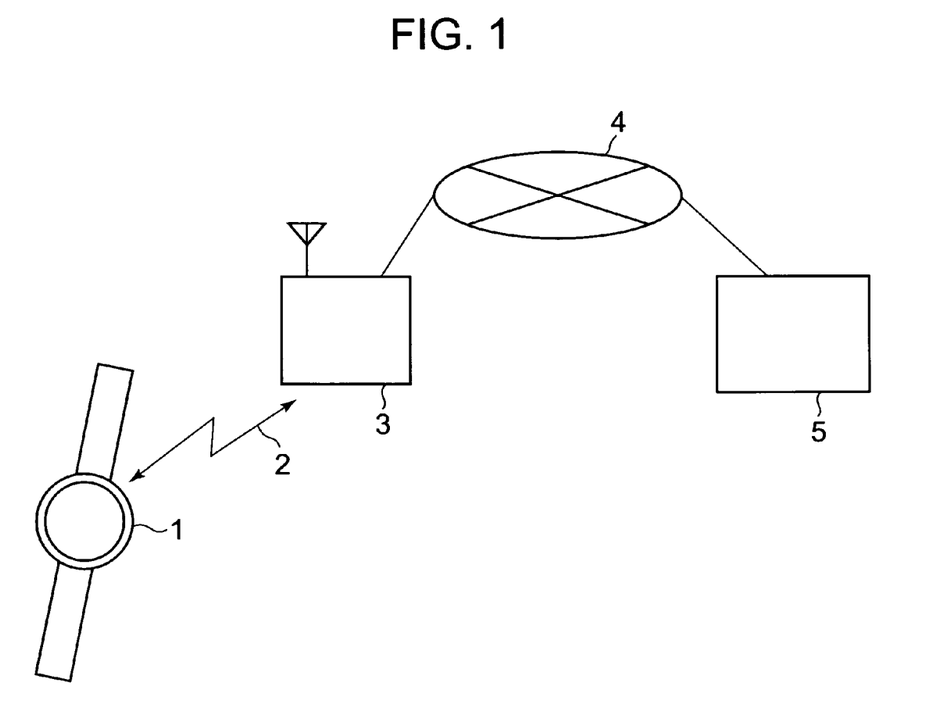
FIG. 1 is a view showing a total constitution of the invention.

FIG. 1 is a view showing a total constitution of the invention. Numeral 1 designates an organism information detecting apparatus for measuring organism information of a subject in accordance with previously determined schedule information. Here, a wrist watch type apparatus is conceived for measuring a pulsation number of a subject. Numeral 5 designates an organism information processing server located at a remote place for collecting organism information data measured by the organism information apparatus 1 to be processed. Numeral 3 designates a wireless communication apparatus for receiving organism information data measured by the organism information detecting apparatus 1 and delivering the data to the server. Numeral 2 designates wireless communication between the organism information detecting apparatus 1 and a wireless communication portion. Numeral 4 designates a communication network between the wireless communication apparatus 3 and the organism information processing server.

Figure 2:
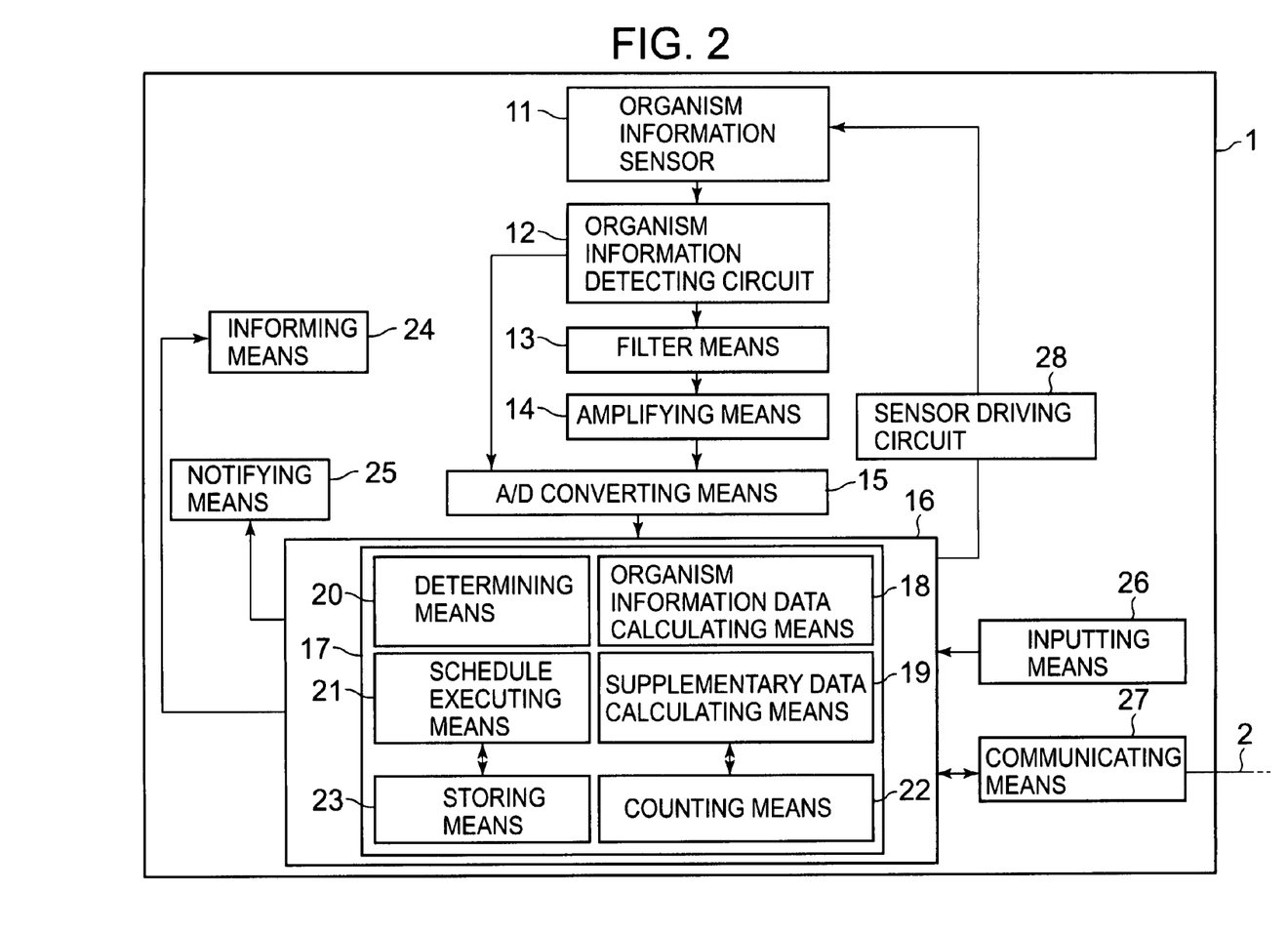
FIG. 2 is a block diagram showing an outline of an organism information detecting apparatus 1.

Next, the organism information detecting apparatus 1 will be explained. FIG. 2 is a block diagram showing an outline of the organism information detecting apparatus 1. Numeral 11 designates an organism information sensor for detecting organism information of a subject. Here, the organism information sensor is a pulse wave sensor for detecting a change in an amount of blood of the artery caused by pulsation of the subject and various sensors of an optical sensor, a piezoelectric element or the like can be used in accordance with a detecting system. Numeral 12 designates an organism information detecting circuit in which the organism information sensor 11 converts a signal of organism information into an organism signal of a voltage level. Numeral 13 designates filter means for extracting a signal (pulse wave signal) caused by a change in the amount of blood of the artery of the subject. Specifically, the filter means is a by path filter for extracting a high frequency component. Numeral 14 designates an amplifying means for amplifying the signal extracted by the filter means 13. Numeral 15 designates A/D converting means for converting the signal amplified by the amplifying means 13 to digital data. The A/D converting means 15 is used also when the organism signal of the organism information detecting circuit 12 into digital data for calculating supplementary data.

Numeral 16 designates CPU of the organism information detecting apparatus. In CPU, there are included operating means 17 for executing various operation, storing means 23 comprising ROM or RAM for temporarily storing data of organism information data, supplementary data, a result of determination or the like, or storing a program for realizing various operation or information necessary for various operation (threshold or the like), counting means 22 for counting a time period for measuring organism information data or the like.

Here, specifically, the operating means 17 includes organism information data calculating means 18 for calculating organism information data (in this case, pulsation number) by using digital data of a signal caused by a change in an amount of blood of the artery of the subject converted by the A/D converting means 15, supplementary data calculating means 19 for calculating supplementary data by using an organism signal converted by the A/D converting means 15, determining means 20 for determining a motion state of the subject who is being measured by evaluating the calculated supplementary data based on a previously determined threshold stored to the storing means 23 and determining a degree of reliability of organism information data based on the motion state, and schedule executing means 21 for realizing to measure organism information in accordance with schedule information received from the organism information processing server, and these are realized by programs stored in the storing means as has been explained above.

Further, CPU 16 is connected to a sensor driving circuit 28 for driving the organism information sensor 11, informing means 24 comprising displaying means, voice means or the like for informing information of organism information data or the like to the subject, notifying means 25 comprising a buzzer, vibrating means or the like for informing emergency information to the subject, inputting means comprising a key, a button or the like for receiving an input from the subject, and communicating means 27 for receiving schedule information from the organism information processing server or returning organism information data and supplementary data as a result of executing the schedule information thereto. The communicating means 27 establishes the wireless communication 2 with the wireless communication apparatus 3 and communicates with the organism information processing server 5 by way of the wireless communication portion 3.

Figure 3:
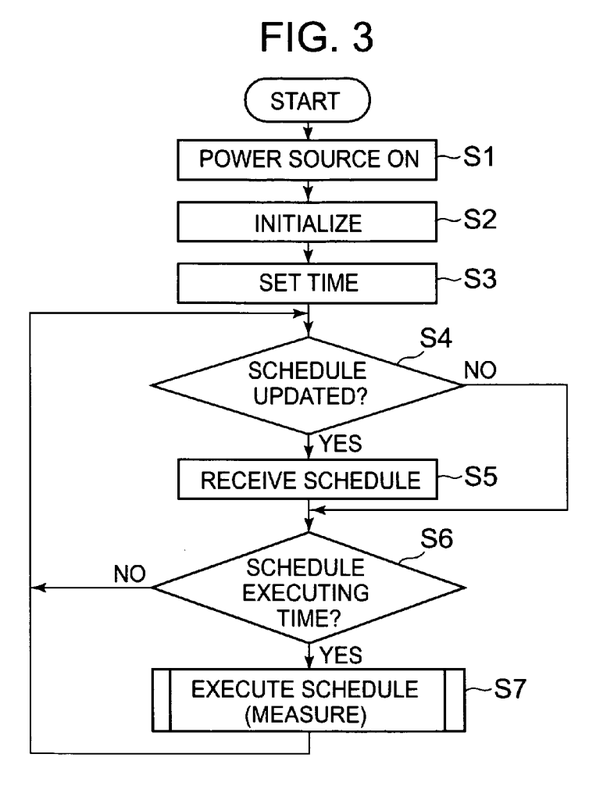
FIG. 3 is a flowchart showing a basic operation of the organism information detecting apparatus 1.

Next, an explanation will be given of a basic operation of detecting organism information by the organism information detecting apparatus 1 shown in FIG. 1 and FIG. 2 and calculating organism information data (pulsation number) in reference to FIG. 3. FIG. 3 is a flowchart showing the basic operation of the organism information detecting apparatus 1. First, when a subject mounts the organism information detecting apparatus 1 on the arm and inputs a power source (step S1), the organism information detecting apparatus 1 initializes a region of the storing means 13 for temporarily storing data of organism information data, supplementary data, a determination result or the like (step S2). Successively, the communicating means 27 establishes communication with the organism information processing server 5 by way of the wireless communication apparatus 3 by establishing wireless communication with the wireless communication apparatus 3, receives current time data from the organism information processing server 5 and makes the organism information processing server 5 and a timer provided to the counting means 25 synchronized with each other (step S3).

Figure 4:
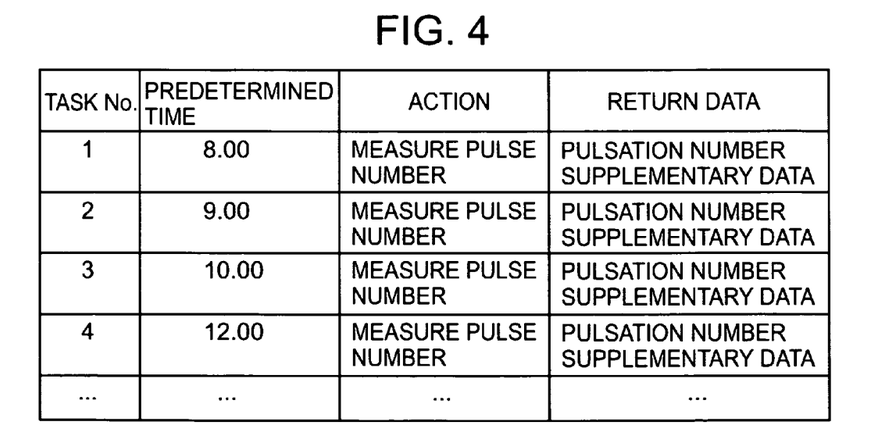
FIG. 4 shows schedule information for rectifying operation of the organism information detecting apparatus 1 formed and tabulated at an organism information processing server 5.

Next, the communicating means 27 inquires of the organism information processing server 5 whether schedule information is updated and receives the schedule information when the schedule information is updated (steps S4, S5). Here, the schedule information will be explained in reference to FIG. 4. The schedule information is information formed by the organism information processing server 5 and tabulated as shown by FIG. 4 for rectifying operation of the organism information detecting apparatus 1. Specifically, the schedule information is information comprising task No., time of executing action (here, time of measuring a pulsation number), content of action executed at the time (here, measurement of pulsation number), data name to be returned as a result of executing the schedule information (here, pulsation number and supplementary data). The schedule information is stored to the storing means 23, and is not erased even when the power source of the organism information detecting apparatus 1 is made OFF, and a content thereof is not changed until the schedule information is updated at steps S4, S5. The schedule information is executed by the schedule executing means 21. That is, the schedule information executing means 21 checks current time indicated by the timer provided to the counting means 22 and schedule information time (step S6), and makes means related to the action (measurement of pulsation number) execute when predetermined time of executing action (predetermined time of measuring pulsation number) is reached (step S7).

Figure 5:
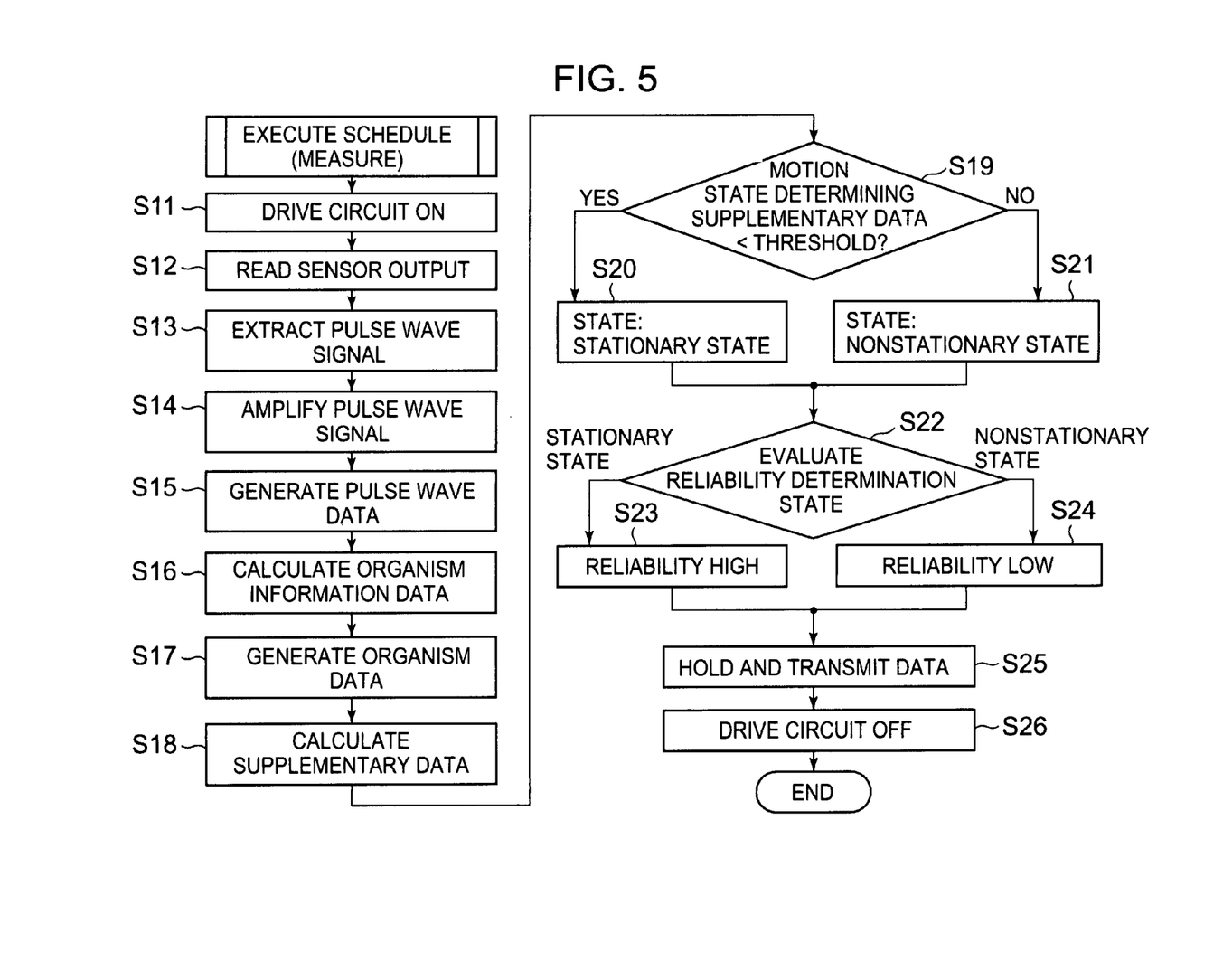
FIG. 5 is a flowchart showing operation of executing the schedule information of the organism information detecting apparatus 1.

Next, an explanation will be given details of operation of the organism information detecting apparatus 1 when the schedule information is executed. FIG. 5 is a flowchart showing operation of executing the schedule information at the organism information detecting apparatus 1. First, at time point of reaching predetermined time of measurement in the schedule information, a power source of the sensor driving circuit 28 of the organism information sensor 11 is made ON (step S11). The power source of the sensor drive circuit 28 is brought into an OFF state at other than time of measurement.

Next, the organism information detecting circuit 12 converts a pulse wave detected by the organism information sensor 11 into an organism signal of a voltage level (step S12).

Next, the organism information data (pulsation number) is calculated by using an organism signal, and an explanation will be given here of a method of calculating the organism information data (pulsation number) from the organism signal in reference to FIG. 6.

Figure 6A:
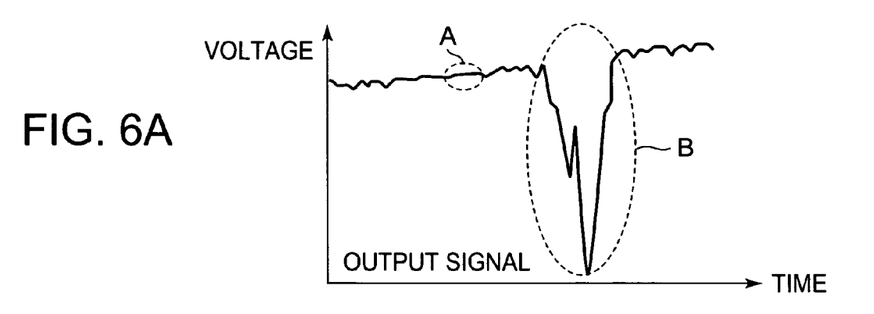
FIG. 6 is a graph showing a change over time of an organism signal and a pulse wave signal of the organism information detecting apparatus 1.
Figure 6B:
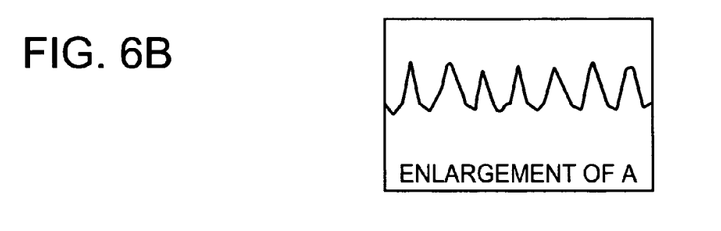

FIG. 6(*a*) is a graph showing a change over time of the organism signal of the organism information detecting apparatus 1. In the drawing, notation A designates the organism signal at a stationary time, and notation B designates the organism signal when the arm mounted with the organism information detecting apparatus 1 is put into motion. FIG. 6(*b*) is a diagram enlarging portion A of FIG. 6(*a*). An amount of blood of the artery of the subject is changed by pulsation and therefore, a pulse wave signal caused by a change in the amount of blood of the artery is varied by a short period similar to pulsation. However, the actual pulse wave signal is extremely smaller than an amount of light transmitted through or reflected by the organism (about 1/1000 or smaller) and therefore, as indicated by portion A of FIG. 6(*a*), the signal can hardly be recognized and can be confirmed by being enlarged as shown by FIG. 6(*b*). Therefore, the organism information data is calculated by a method of extracting the signal (pulse wave signal) which is varied by an extremely small amount from the organism signal, amplifying the signal and subjecting the signal to a previously determined processing.

First, the pulse wave signal is extracted from the organism signal by using the filter means 13 (step S13). Next, the extracted pulse wave signal is amplified by the amplifying means 14 (step S14). Next, pulse wave data is generated by digitizing the amplified signal by the A/D converting means 15 and sampling the signal for a previously determined time period by previously determined sampling frequency (step S15). For example, 128 pieces of pulse wave data are generated by sampling the signal for 16 seconds by 8 Hz.

Further, at the organism information data calculating means 18, the organism information data (pulsation number) is calculated by using the pulse wave data (step S16). The pulsation number is calculated by subjecting the pulse wave data to a frequency analysis. Further, the method of calculating the pulsation number is not limited to the frequency analysis but, for example, a number of times of peaks of the pulse wave signal in 1 minute may be counted or the like.

Figure 10:
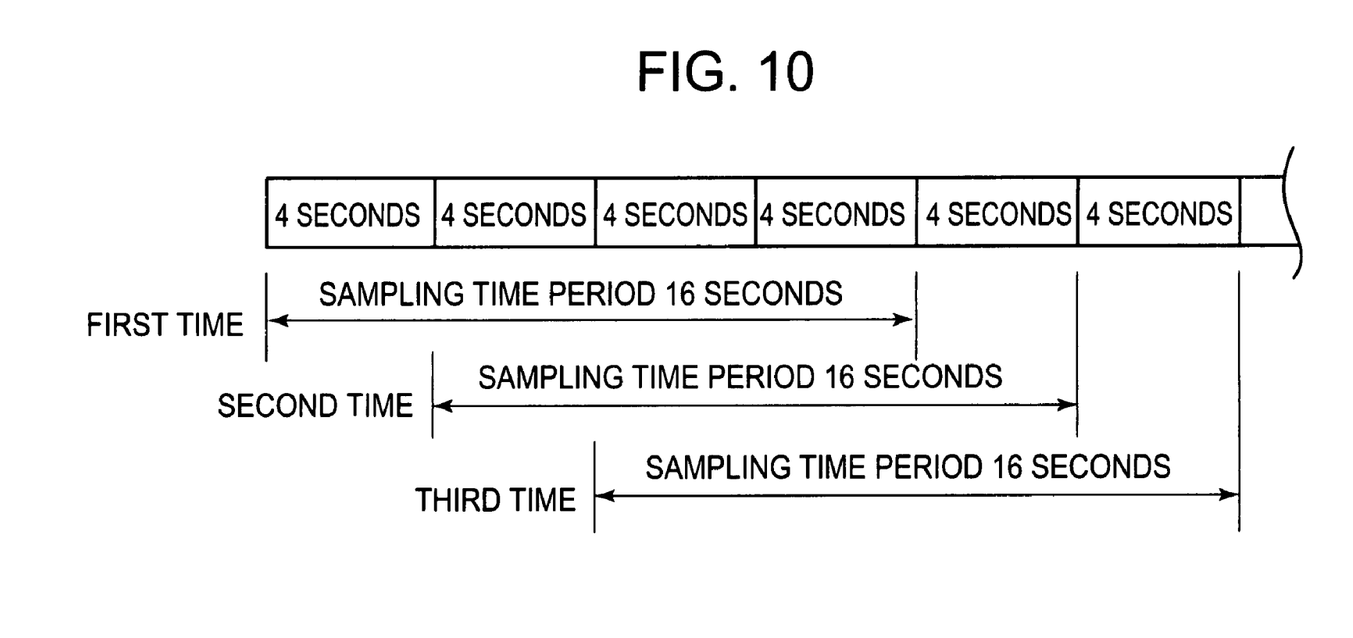
FIG. 10 shows an example showing a timing of sampling a pulsation measurement.

Further, when the pulsation number is continuously calculated by continuously detecting the organism information for a long period of time, a certain initial time period of sampling data of a first time (time period of 1/m of sampling time period, notation m indicates an integer) may be deleted and in measurement of a second time, only data of a time period which is deficient may be measured. FIG. 10 shows an example of timings of sampling in that case. Top 4 seconds of sampling data of 16 seconds of a first time are deleted and in measurement of a second time, only sampling data of 4 seconds which is deficient is measured. By adopting such a method, it is not necessary to execute all of measurement necessary for calculating a pulse number at every time but a display in a short time period can be updated (here, 4 seconds interval) and therefore, a user can confirm a current state without awaiting for a long period of time.

Next, there is calculated supplementary data of calculated organism information data (pulsation number) indicating a motion state of the subject in measurement, and an explanation will be given here of a method of calculating the supplementary data from the organism signal in reference to FIG. 7.

Figure 7A:
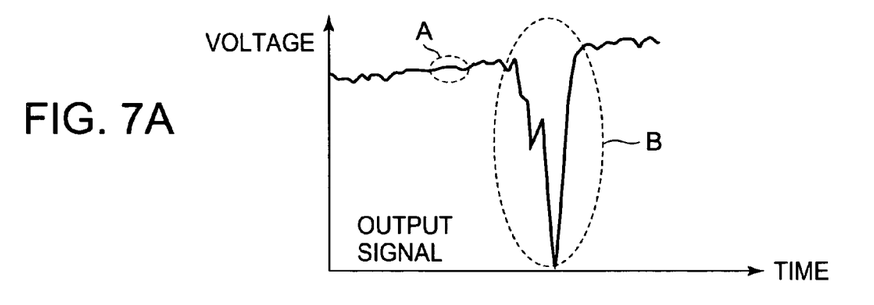
FIG. 7 illustrates graphs showing the change over time of the organism signal and an amount of a variation of the organism signal per time.
Figure 7B:
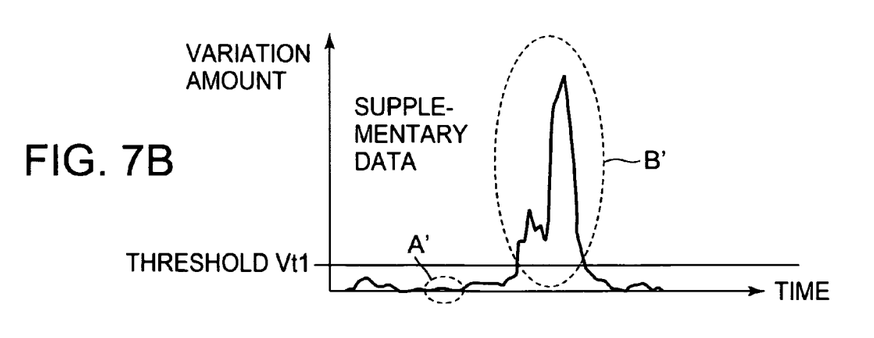

FIG. 7(*a*) is a graph showing a change over time of the organism signal of the organism information detecting apparatus 1. In the drawing, notation A designates the organism signal at stationary time, notation B designates the organism signal when the arm mounted with the organism information detecting apparatus 1 is put into motion. FIG. 7(*b*) is a graph showing an amount of a variation per time of the organism signal in FIG. 7(*a*). A pulse wave component of the organism signal caused by a change in the amount of blood of the artery of the subject is extremely small and therefore, the organism signal per se can be regarded as a signal caused by a physical movement of the subject, a change in an amount of blood of the vein or the like, The organism signal is provided with a characteristic in which the organism signal is gradually varied by a very long period of several tens seconds to several minutes owing to a change in the amount of blood of the vein of the subject and is not varied rapidly in a short period of time. However, when the subject is put into motion, as indicated by portion B of FIG. 7(*a*), the organism signal is significantly varied even in a short period of time. This signifies that by observing an amount of a variation in the organism signal per a time period shorter than a period of a change in an amount of blood of the vein of the subject, motion of the subject brought about when the organism information is detected can be confirmed without being influenced by the change in the amount of blood of the vein. The behavior is shown by FIG. 7(*b*).

An amount of a variation per time of the organism signal in correspondence with portion B of FIG. 7(*a*) is portion B' in FIG. 7(*b*), showing a very large value. On the other hand, an amount of a variation per time of the organism signal in correspondence with portion A of FIG. 7(*a*) is portion A' in FIG. 7(*b*), showing an extremely small value. Further, although the organism signal tends to rise gradually as a whole in FIG. 7(*a*), the influence is not observed in FIG. 7(*b*). In this way, the amount of the variation in the organism signal per a time period shorter than the period of the change in the amount of blood of the vein of the subject precisely expresses the motion state of the subject and therefore, the characteristic is applied for calculating the supplementary data.

First, the organism data is generated by digitizing the organism signal by the A/D converting means 15 and sampling the signal for a previously determined time period by a previously determined sampling frequency (step S17). Here, the sampling period is constituted by a sampling period the same as that in the case of the organism information data for calculating the supplementary data in correspondence with the organism information data explained above. Further, as the sampling frequency, there is selected a frequency constituting a period shorter than the period of the change in the amount of blood of the artery of the subject. Here, for example, the sampling frequency (8 Hz) the same as that in the case of the organism information data is selected.

Next, the supplementary data is calculated at the supplementary data calculating means 19 (step S18). The supplementary data is an average value of the amount of the variation per time of the organism data in one sampling time period. The supplementary data is specifically defined as shown by Equation 1 by constituting "per time" by a data sampling interval t (=1/sampling frequency=0.125 second) of the organism data and constituting "variation amount" by an absolute value of a difference of organism data contiguous to each other of sampled organism data (voltage value).

$$\text{supplementary data} = \left\{ \sum_{i=2}^{n} |V_i - V_{i-1}| \right\} / (n-1) \qquad \text{Equation 1}$$

Here, notation n designates a data number of the organism data provided during the sampling time period and is a value constituted by dividing the sampling time period t of the organism information by the sampling interval t of the organism data. Specifically, n=T/t=16 seconds/0.125 second=128. Further, notation Vi designates an i-th organism data (voltage value).

Further, step S16 shows an example of away of measurement when the organism information is detected continuously for a long period of time and the pulsation number is continuously calculated, and Equation 2 can be used as an equation when the supplementary data is calculated in accordance therewith.

$$\text{supplementary data} = \left[ \sum_{k=1}^{m} \left\{ \sum_{i=2}^{b} |V_{i+b(k-1)} - V_{i-1+b(k-1)}| \right\} / (b-1) \right] / m \qquad \text{Equation 2}$$

$$b = n/m$$

Equation 2 is an equation indicating that the sampling time period T is equally divided into m pieces of blocks, an average value of a variation amount per time is calculated for each block, and an average value of the average value is further calculated. Notation b signifies a number of pieces of organism data included in 1 block. Specifically, m (number of pieces of blocks)=T seconds/4 seconds=16 seconds/4 seconds=4, n (total data number)=T/t=16 seconds/0.125 second=128, b (data number included in 1 block)=n/m=128/4=32 as shown by Equation 3.

$$\text{supplementary data} = \left[\left\{\sum_{k=1}^{4}\sum_{i=2}^{32}|V_{i+32(k-1)} - V_{i-1+32(k-1)}|\right\}/31\right]/4 \quad \text{Equation 3}$$

Figure 11:
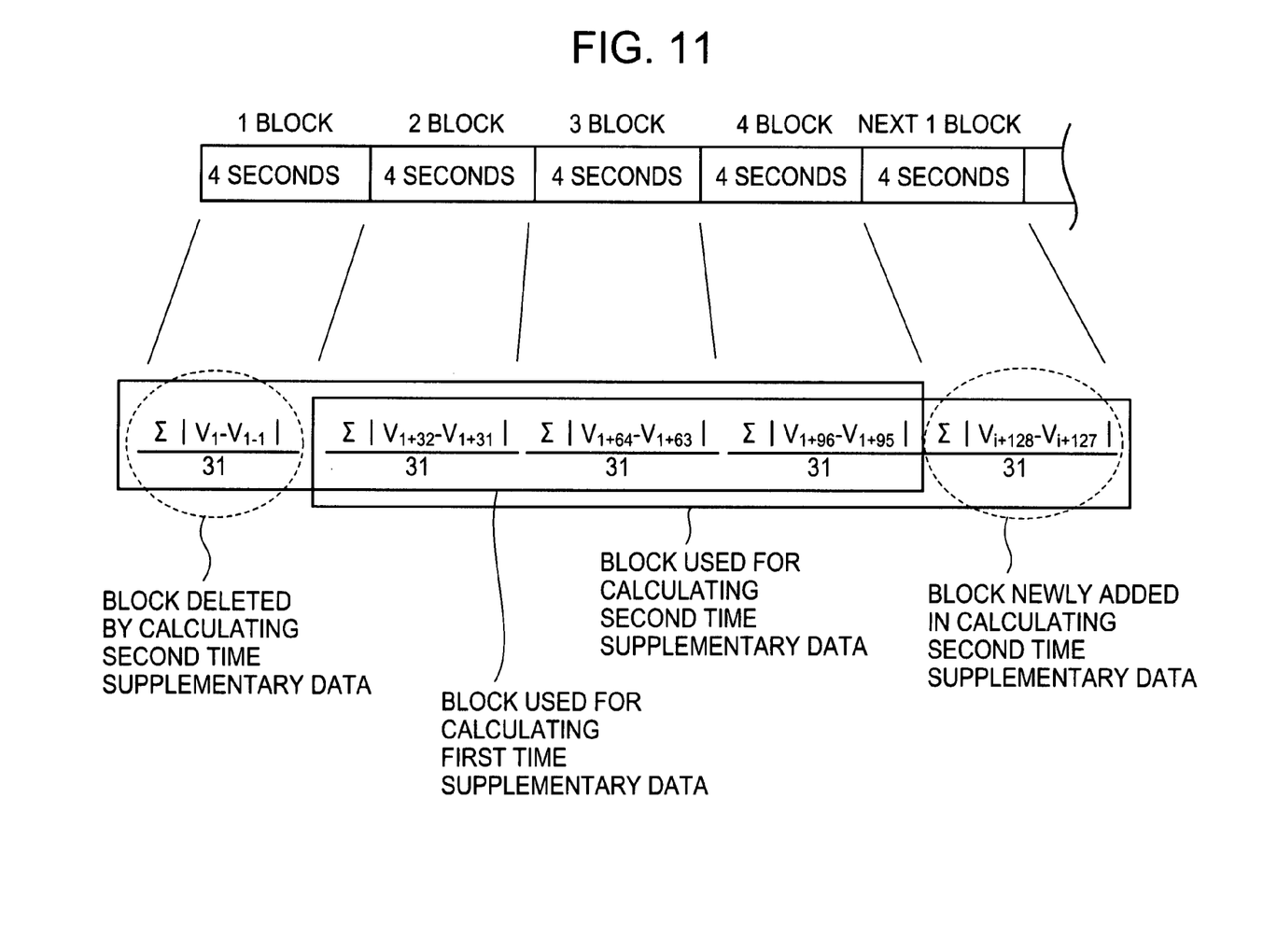
FIG. 11 is diagram for explaining a method of calculating an average value of the amount of the variation per time calculated in accordance with the timing of sampling the pulsation measurement.

By adopting such an equation, a calculation corresponding with the organism information data can be executed only by a simple operation based on an average value of the variation amount per time of each block. FIG. 11 shows the calculation. As shown by the drawing, at first time of calculating the supplementary data, the supplementary data can be calculated by averaging the average values of the variation amounts per time of 1 block, 2 block, 3 block, 4 block. In calculating the supplementary data at second time, in order to delete average value of the variation amount per time of 1 block of first time in 4 pieces of blocks used in calculation at a preceding time and newly add 1 block deficient in calculating the supplementary data, the average value of the variation amount per time of a successive 1 block is calculated. Further, by averaging the average values of the variation amounts per time of 2 block, 3 block, 4 block, successive 1 block, the supplementary data can be calculated.

Next, the motion state of the subject is determined based on the calculated supplementary data at the determining means 20 (step S19). In the determination, a threshold which is previously determined and stored to the storing means 23 is read to be used. The threshold can be calculated by, for example, previously calculating supplementary data at stationary time and motion time of the subject and based on the actual motion state and a tendency of the supplementary data. For example, FIG. 7(*b*) is a graph of supplementary data at stationary time and motion time and therefore, based on the graph, an upper limit of a value which the supplementary data at stationary time can take can be determined as a threshold Vt1. Further, here, although the threshold is one of Vt1, the threshold is not limited thereto but may be set by an arbitrary number by an arbitrary value in accordance with the subject and the content of motion.

In determining the motion state, when the supplementary data is smaller than the threshold Vt1, it can be determined that the subject is brought into the stationary state (step S20). However, when the supplementary data is equal to or larger than the threshold Vt1, it can be determined that the subject is brought into a nonstationary state (step S21).

Next, a reliability degree of the calculated organism information data (pulsation number) is determined (step S22). In determination, there is used a relationship of "motion state and reliability degree of organism information data" stored to the storing means 23. Generally, it can be regarded that the organism information data measured when the subject is stationary is provided with a high reliability degree and it can be regarded that the organism information data measured when the subject is put into motion is provided with a low reliability degree by being influenced by noise of physical movement or the like. Here, based on the way of thinking, the storing means 23 is stored with information that the organism information data is provided with the "high reliability degree" when the motion state is a stationary state and is provided with the "low reliability degree" when the motion state is a nonstationary state. Therefore, when the motion state is the stationary state, it is determined that the organism information data is provided with the "high reliability degree" (step S23) and when the motion state is brought into the nonstationary state, the organism information data is provided with the "low reliability degree" (step S24). Further, although here, there are two kinds of the motion states of the stationary state and the nonstationary state and therefore, there are two kinds of determination of the reliability degree of "high reliability degree" and "low reliability degree", the reliability can be determined by the arbitrary kinds of determinations by setting the thresholds for determining the motion states as described above by an arbitrary value and by an arbitrary number.

Next, the calculated organism information data and the calculated supplementary data are stored by being related to each other and returned to the organism information processing server 5 in accordance with the schedule information (step S25). At this occasion, also the determined motion state and the determined reliability degree may be stored and transmitted by being related to each other.

Further, a series of operation in accordance with the schedule information is finished by making the power source of the sensor driving circuit 28 of the organism information sensor 11 OFF.

In this way, according to the embodiment, there can be provided the supplementary data capable of determining the motion state of the subject when the organism information is detected, that is, whether the subject is brought into the stationary state along with the organism information data. Further, by observing the supplementary data, it can be determined whether the organism information data is provided with a high reliability degree. Further, the determination can be carried out without using other organism information detecting means in addition thereto.

Further, although according to the embodiment, an explanation has been given of a series of flow until determining the reliability degree of the organism information data after detecting the organism information of the subject by the organism information detecting means, for example, the motion state when the organism information is detected can be determined and the reliability degree of the organism information data can be determined by, for example, storing digital data of the organism signal in a distal end of the organism information and thereafter reading the stored digital data.

Second Embodiment

Next, an explanation will be given of operation of the organism information processing server 5 for receiving the organism information data and supplementary data from the organism information detecting apparatus 1 as a second embodiment of the invention in reference to FIG. 8.

Figure 8:
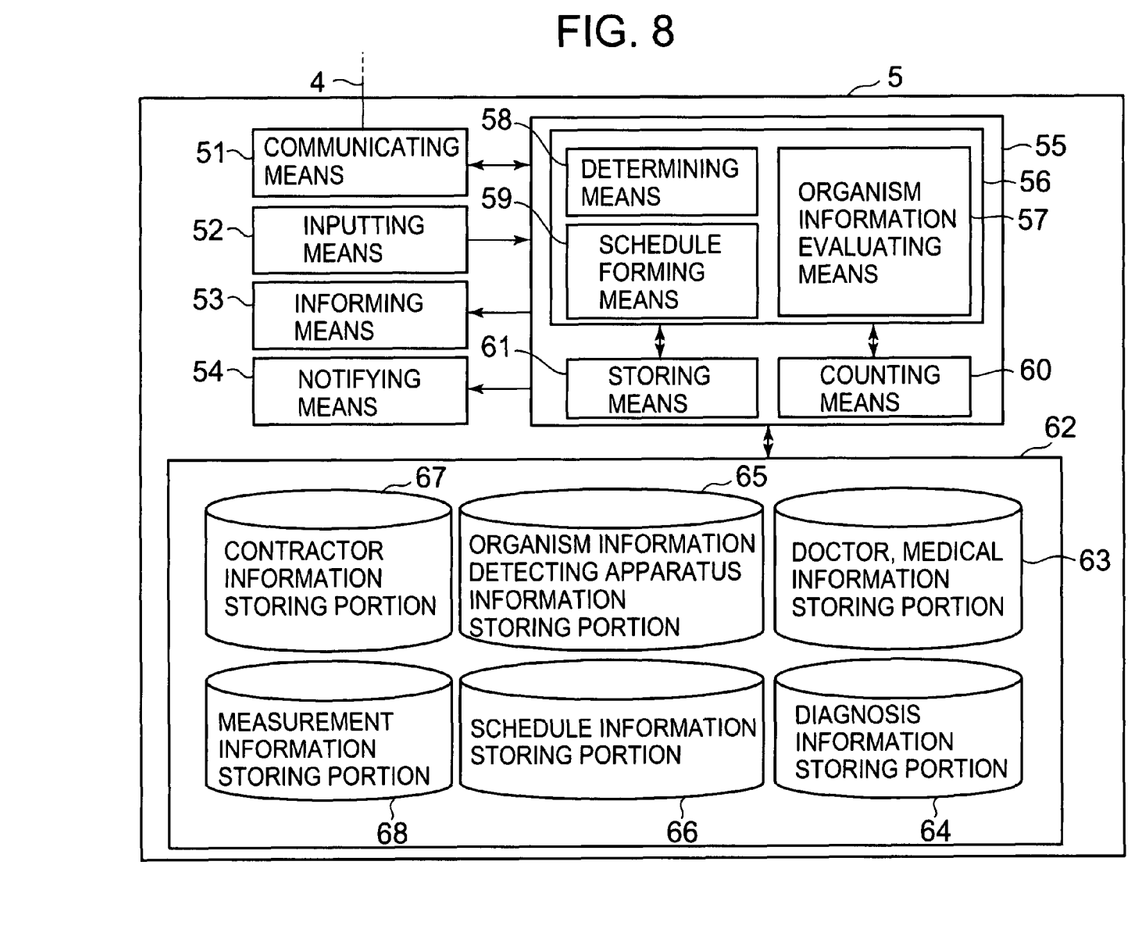
FIG. 8 is a block diagram showing an outline of the organism information processing server 5.

FIG. 8 is a block diagram showing an outline of the organism information processing server 5. Numeral 51 designates communicating means for transmitting and receiving information or the like to and from the organism information detecting apparatus 1 by establishing communication with the wireless communication apparatus 3 on the communication network 4. Numeral 52 designates inputting means for receiving an input from an operator or the like of the server. Numeral 53 designates informing means comprising display means or voice means or the like for informing the organism information data received from the organism information detecting apparatus 1, or previously stored data. Numeral 54 designates notifying means comprising a buzzer or the like for notifying emergency information to the operator or the like of the server. These are connected to CPU 55.

Numeral 55 designates CPU including operating means 55 for executing various operation, storing means 61 for temporarily storing information of data, a threshold or the like used in operation, or data or the like generated in operation, storing a program or the like for realizing various operation and comprising ROM or RAM, and counting means 60 having a reference timer for providing reference time of the timer of all of the organism information detecting apparatus 1 under control.

Here, the calculating means 55 includes organism information evaluating means 57 for evaluating a health state of the subject by using the organism information data received from the organism information detecting apparatus 1 or previously stored data, determining means 58 for determining the motion state of the subject in measurement by evaluating the supplementary data or the previously stored data received from the organism information detecting apparatus 1 based on a threshold determined for each of the subjects and determining the reliability degree of the organism information data based on the motion state, and schedule information forming means 59 for forming schedule information transmitted to the organism information detecting apparatus 1.

CPU 55 is connected to the storing portion 62 stored with various information and information of the storing portion 62 can be surveyed or updated in a secured environment.

The storing portion 62 includes a doctor, physical information storing portion 63 for storing information with regard to a specialist at each area for respective names of diseases and information with regard to names of diseases and symptoms or the like thereof which can be provided to the subject, a diagnosis information storing portion 64 for storing information with regard to a result of evaluating and diagnosing the health state of the subject based on the organism information data, an organism information detecting apparatus information storing portion 65 for storing information of a name, a type No., fabrication year, month, date of the organism information detecting apparatus 1 owned by the subject, a schedule information storing portion 66 for storing the schedule information transmitted to the organism information detecting apparatus 1, a contractor information storing portion 67 for storing personal information of an identification No., name, address, name (number) of used organism information detecting apparatus of a contractor (subject) contracted with the organism information detecting system or the like, a measurement information storing portion 68 for storing the organism information data, the supplementary data received from the organism information detecting apparatus 1, the threshold used for processing the supplementary data, a result of determining the motion state or the like.

The organism information processing server 5 executes operation similar to that of steps S19 through S24 of the flowchart of FIG. 5 showing operation of executing the schedule information at the organism information detecting apparatus 1 after receiving the organism information data and supplementary data from the organism information detecting apparatus 1. That is, the organism information processing server 5 calculates the motion state of the subject and the reliability degree of the organism data based on the received supplementary data. Here, the organism information processing server 5 includes past organism information data of the subject, information of the diagnosis result, medical information or the like as described above and therefore, the organism information processing server 5 can variously processes also the supplementary data of the organism information data. For example, the organism information processing server 5 can execute a processing combined with various information of setting a highly accurate threshold by executing a statistical processing with regard to all the data by using all of the organism information data immediately after receiving from the organism information detecting apparatus 1 and the past organism information data, calculating the motion state and the reliability degree based on the threshold, setting again the threshold based on a tendency of a disease affected to the subject, calculating the motion state and the reliability degree and the like.

In this way, the determination of the motion state and the reliability degree with higher certainty combined with various information can be executed by processing the supplementary data by the organism information processing server 5 and therefore, the diagnosis using only the organism information data having a higher reliability degree can be executed and the accurate diagnosis can be executed.

Third Embodiment

Next, an explanation will be given of an application example for controlling operation of the organism information detecting apparatus 1 by using the motion state constituting the result of determining the supplementary data as a third embodiment of the invention in reference to FIG. 9.

Figure 9:
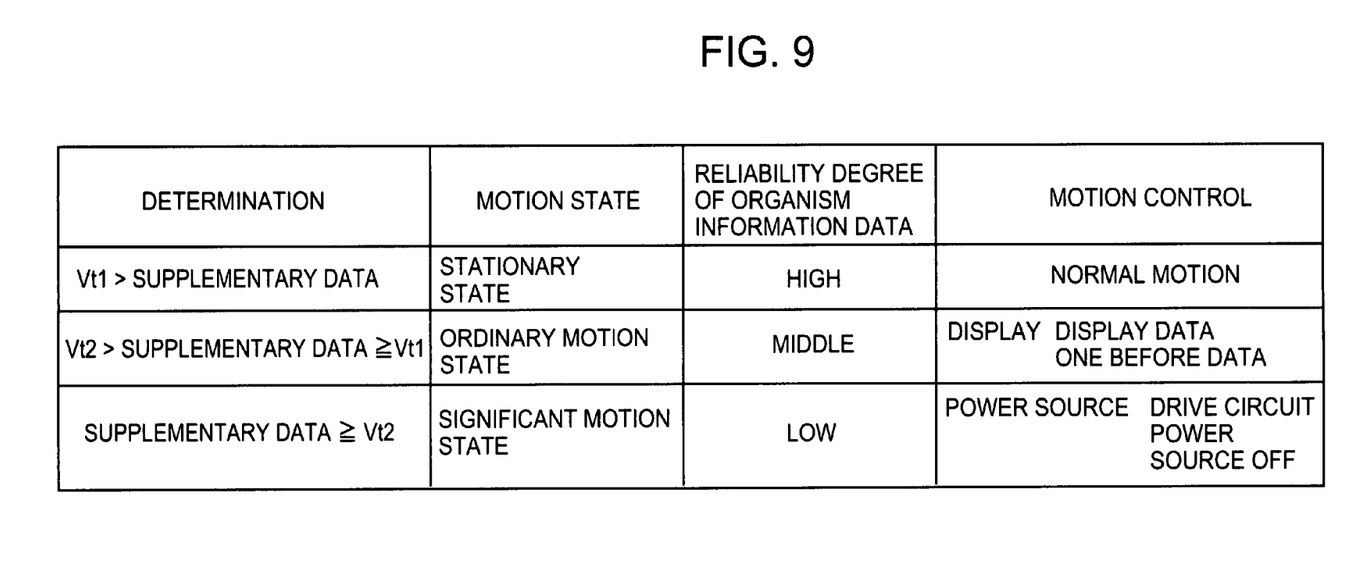
FIG. 9 is a table for determination used in the invention.

FIG. 9 is a table for determination showing the threshold of the supplementary data, the motion data in correspondence with the threshold, the reliability degree of the organism information data in correspondence with the motion state, and a content of controlling operation of the organism information detecting apparatus 1 in correspondence with the reliability degree. The table which is previously formed by the organism information processing server 5 can be received by the organism information detecting apparatus 1, stored to the storing means 23 and read as needed to be used.

When the table for determination of FIG. 9 is used, for example, when the supplementary data is smaller than Vt1, it can be regarded that the motion state is the stationary state and the reliability degree of the organism information data is high and therefore, the organism information detecting apparatus 1 can be operated as normal.

Further, when the supplementary data is equal to or larger than Vt1 and smaller than Vt2, it can be regarded that the motion state is an ordinary motion state and the reliability degree of the organism information data is middle and the display data is controlled such that data before the data having the high reliability degree is displayed. It is an object thereof to prevent a physical stress from being applied to the subject by displaying abnormal data caused by the motion state (not caused by abnormality of the body). Further, when the supplementary data continues such a condition for a while, the subject can be urged to restrain from the motion by making a display screen OFF or the like.

Further, when the supplementary data is equal to or larger than Vt2, it can be regarded that the motion state is a significant motion state and the reliability degree of the organism information data is low and a power source of the organism information detecting circuit is controlled to be OFF. It is also an object thereof to save power by stopping a wasteful measurement since a measured value under a state having the low reliability degree is devoid of credibility. Further, not only the power source of the circuit can be made OFF but also the power source can be made OFF after informing that the measurement is executed again.

In this way, operation of the organism information detecting apparatus 1 can be controlled by using a result of determining the motion state, for example, the subject can be urged to execute the measurement again for providing the organism information data having a higher reliability degree. Further, when it is determined that the subject executes the significant motion, by making the power source of the organism information detecting means OFF, the wasteful measurement without the reliability degree can be prevented and power can be saved.

Further, the motion state of the organism information may be determined by recording the program for realizing respective functions of the supplementary data calculating means 19, the determining means 20 by a record medium readable by a computer and executing the program recorded to the record medium by making the computer system read the program. Further, the "computer system" mentioned here includes OS and a hardware of peripheral apparatus or the like. Further, the "computer readable recording medium" refers to a transportable medium of a flexible disk, an opt-magnetical disk, ROM, CD-ROM or the like, a storing apparatus of a hard disk or the like included in the computer system. Further, the "computer readable record medium" includes a medium holding the program for a constant period of time such as a server when the program is transmitted by way of a communication network of a network of internet or the like, a telephone network or the like, or a volatile memory (RAM) at inside of the computer system constituting a client.

Further, the program may be transmitted from the computer system storing the program in the storing apparatus or the like to other computer system by way of a transmission medium, or a transmission wave in the transmission medium. Here, the "transmission medium" for transmitting the program refers to a medium having a function of transmitting information such as a network (communication network) of internet or the like or a communication network (communication line) of a telephone network or the like. Further, the program may be for realizing a portion of the above-described function. Further, the program may be a program capable of being realized by being combined with a program already recorded to the computer system, or being combined with the hardware already present in the computer system, a so-to-speak difference file (difference program).

In this way, according to the invention, there can be provided the supplementary data capable of determining the motion state of the subject, that is, whether the subject is brought into the stationary state when the organism information is detected along with the organism information data and therefore, it can be determined whether the organism information data is provided with the reliability degree by observing the supplementary data. Further, the determination can be executed without using other organism information detecting means in addition thereto.

Further, as a derivative effect of the invention, by informing the determination result to the subject, the subject can be urged to execute measurement again for providing the organism information data having a higher reliability degree. Further, when it is determined that the subject executes significant motion, by making the power source of the organism information detecting means OFF, a wasteful measurement without reliability degree can be prevented and power can be saved.

INDUSTRIAL APPLICABILITY

The invention can be adapted to the organism information detecting apparatus for detecting the organism information data.

The invention claimed is:

1. An organism information detecting apparatus for detecting organism information of a subject, the organism information detecting apparatus comprising:
   detecting means configured to come into contact with a subject for detecting organism information of the subject for a predetermined sampling time period, determining a motion state of the subject when the organism information is detected, and outputting an organism signal;
   first calculating means for processing the organism signal to calculate organism information data, the detecting means determining a reliability degree of the organism information data based on whether the determined motion state of the subject is a previously determined motion state;
   second calculating means for calculating an average value of the amount of variation per time of data obtained by digitizing the organism signal, the average value being data supplementary to the organism information data, and the detecting means determining the motion state of the subject based on whether the supplementary data exceeds a previously determined threshold; and
   storing means for storing the organism information data and the supplementary data such that the organism information data and the supplementary data are associated with one another.

2. An organism information detecting apparatus according to claim 1; further comprising:
   informing means for informing the organism information data to the subject; and
   informing data determining means for determining the organism information data informed by the informing means based on whether the determined reliability degree is a previously determined reliability degree.

3. An organism information detecting apparatus according to claim 2; wherein the organism information is a waveform of the subject's artery; and wherein the detecting means subjects digital data of a component of a pulse wave included in the organism signal of the sampling time period to a frequency analysis and calculates a pulsation number as the organism information data.

4. An organism information detecting apparatus according to claim 2; further comprising:
   power source controlling means for controlling ON/OFF of a power source of the detecting means based on whether the determined reliability degree is the previously determined reliability degree.

5. An organism information detecting apparatus according to claim 4; wherein the organism information is a waveform of the subject's artery; and wherein the detecting means subjects digital data of a component of a pulse wave included in the organism signal of the sampling time period to a frequency analysis and calculates a pulsation number as the organism information data.

6. An organism information detecting apparatus according to claim 1; further comprising:
   communicating means for communicating information with an organism information processing server disposed at a remote
   schedule executing means for detecting the organism information based on schedule information from the organism information processing server received by the communicating means and corresponding to measured organism information;

wherein the communicating means transmits the organism information data and the supplementary data to the organism information processing server as a result of result of executing the schedule executing means.

7. An organism information detecting apparatus according to claim 6; wherein the organism information is a waveform of the subject's artery; and wherein the detecting means subjects digital data of a component of a pulse wave included in the organism signal of the sampling time period to a frequency analysis and calculates a pulsation number as the organism information data.

8. An organism information detecting apparatus according to claim 1; wherein the detecting apparatus equally divides the sampling time period into a plurality of pieces of block time periods and defines the sampling time period at and after a second time by erasing an oldest one block time period in the sampling time period at a preceding time and adding one block time period for a new measurement; and wherein the second calculating means calculates an average value of each of the block time periods of the variation amount per time of the data constituted by digitizing the organism signal and calculating an average value of the average values of the respective block time periods as the supplementary data in the sampling time period.

9. An organism information detecting apparatus according to claim 8; wherein the organism information is a waveform of the subject's artery; and wherein the detecting means subjects digital data of a component of a pulse wave included in the organism signal of the sampling time period to a frequency analysis and calculates a pulsation number as the organism information data.

10. An organism information detecting apparatus according to claim 1; wherein the organism information is a waveform of the subject's artery; and wherein the detecting means subjects digital data of a component of a pulse wave included in the organism signal of the sampling time period to a frequency analysis and calculates a pulsation number as the organism information data.

11. An organism information processing method for an organism information detecting apparatus that detects organism information of a subject, the organism information processing method comprising:
   a step of bringing the organism information detecting apparatus into contact with a subject to detect the organism information of the subject for a predetermined sampling time period, determine by a determining means a motion state of the subject when the organism information is detected, and output an organism signal;
   a step of processing the organism signal to calculate organism information data by an organism information data calculating means, a reliability degree of the organism information data being determined based on whether the determined motion state of the subject is a previously determined motion state by the determining means;
   a step of calculating an average value of the amount of variation per time of data obtained by digitizing the organism signal, the average value being data supplementary to the organism information data by the supplementary data calculating means, and the motion state of the subject being determined based on whether the supplementary data exceeds a previously determined threshold by the determining means; and
   a step of storing by a storing means the organism information data and the supplementary data such that the organism information data and the supplementary data are associated with one another.

12. An organism information processing method according to claim 11; wherein the organism information is a waveform of the subject's artery; and wherein the step of calculating the organism information data comprises subjecting digital data of a component of a pulse wave included in the organism signal to a frequency analysis and calculating a pulsation number as organism information data.

13. An organism information processing server for receiving information from an organism information detecting apparatus for detecting organism information of the subject for a predetermined sampling time period and outputting an organism signal, processing the organism signal to calculate organism information data, and calculating an average value of the amount of variation per time of data obtained by digitizing the organism signal, the average value being data supplementary to the organism information data, the organism information processing server executing a previously determined processing operation to the information received from the organism information detecting apparatus, the organism information processing server comprising:
   communicating means for receiving the organism information data and the supplementary data from the organism information detecting apparatus;
   storing means for storing the organism information data and the supplementary data such that the organism information data and the supplementary data are associated with one another;
   motion state determining means for determining a motion state of the subject when the organism information is detected based on whether the supplementary data exceeds a previously determined threshold; and
   reliability degree determining means for determining a reliability degree of the organism information data associated with the supplementary data based on whether the motion state determined by the motion state determining means is a previous determined motion state.

14. An organism information detecting system comprising: an organism information detecting apparatus for detecting organism information of a subject; and an organism information processing server for receiving the organism information from the organism information detecting apparatus and executing a previously determined processing operation to the information received from the organism information detecting apparatus;
   wherein the organism information detecting apparatus comprises:
      organism information detecting means that is configured to come into contact with a subject for detecting organism information of the subject for a predetermined sampling time period and outputting an organism signal;
      organism information data calculating means for processing the organism signal to calculate organism information data;
      supplementary data calculating means for calculating an average value of the amount of variation per time of data obtained by digitizing the organism signal, the average value being data supplementary to the organism information data; and
      transmitting means for associating to one another the organism information data and the supplementary data to be transmitted to the organism information processing server; and wherein the organism information processing server comprises:
- receiving means for receiving the organism information data and the supplementary data from the organism information detecting apparatus;
- data storing means for storing the organism information data and the supplementary data such that the organism information data and the supplementary data are associated with one another;
- motion state determining means for determining a motion state of the subject when the organism information is detected based on whether the supplementary data exceeds a previously determined threshold; and
- reliability degree determining means for determining a reliability degree of the organic information data associated with the supplementary data based on whether the motion state determined by the motion state determining means is a previously determined motion state.

15. An organism information processing method comprising:
- a step of communicating information with an organism information detecting apparatus that detects organism information of a subject for a predetermined sampling time period and outputs an organism signal, processes the organism signal to calculate organism information data, and calculates an average value of the amount of variation per time of data obtained by digitizing the organism signal, the average value being data supplementary to the organism information data;
- a step of storing by a storing means the organism information data and the supplementary data such that the organism information data and the supplementary data are associated with one another;
- a step of determining by a determining means a motion state of the subject when the organism information is detected based on whether the supplementary data exceeds a previously determined threshold; and
- a step of determining a reliability degree of the organism information data associated with the supplementary data based on whether the motion state is a previously determined motion state by the determining means.

16. An organism information processing method used in an organism information detecting system comprising an organism information detecting apparatus for detecting organism information of a subject, and an organism information processing server for executing a previously determined processing operation to the information received from the organism information detecting apparatus;
wherein the organism information detecting apparatus executes a method comprising:
- a step of bringing the organism information detecting apparatus into contact with the subject to detect the organism information of the subject for a predetermined sampling time period and to output an organism signal;
- a step of processing the organism signal to calculate organism information data;
- a step of calculating an average value of the amount of variation per time of data obtained by digitizing the organism signal, the average value being data supplementary to the organism information data; and
- a step of associating the organism information data and the supplementary data to one another for transmission to the information processing server; and wherein the organism information processing server executes a method comprising:
- a step of storing the organism information data and the supplementary data received from the organism information detecting apparatus such that the organism information data and the supplementary data are associated with one another;
- a step of determining a motion state of the subject when the organism information is detected based on whether the supplementary data exceeds a previously determined threshold; and
- a step of determining a reliability degree of the organism information data associated with the supplementary data based on whether the motion state is a previously determined motion state.

17. A motion state determining method of determining a motion state of a subject when organism information is detected in an organism information detecting apparatus comprising organism information detecting means that is brought into contact with the subject for detecting the organism information of the subject, the motion state determining method comprising:
- a step of acquiring data by digitizing using an A/D converter an organism signal outputted by the organism information detecting means during a previously determined sampling time period outputted by the organism information detecting means;
- a step of calculating by a supplementary data calculating means an average value of a variation amount per time of the data; and
- a step of determining by a determining means the motion state of the subject when the organism information is detected based on whether the average value of the variation amount exceeds a previously determined threshold.

18. A reliability degree determining method for determining a reliability degree of organism information in an organism information detecting apparatus comprising organism information detecting means that is brought into contact with a subject for detecting the organism information of the subject, the reliability degree determining method comprising:
- a step of acquiring data by digitizing using an A/D converter an organism signal outputted by the organism information detecting means during a previously determined sampling time period outputted by the organism information detecting means;
- a step of calculating by a supplementary data calculating means an average value of a variation amount per time of the data;
- a step of determining by a determining means a motion state of the subject when the organism information is detected based on whether the average value of the variation amount exceeds a previously determined threshold; and
- a step of determining a reliability of the organism information based on whether the motion state is a previously determined motion state by the determining means.

19. A non-transitory computer readable medium having embodied thereon computer readable instructions which, when executed by a computer, causes the computer to realize a method of determining a motion state of a subject utilizing digital data of an organism signal outputted by organism information detecting means of an organism information detecting apparatus that detects organism information of the subject by being brought into contact with the subject and corresponding to the organism signal, the method comprising:

reading the digital data;
calculating an average value of a variation amount per time of the digital data; and
determining the motion state of the subject when the organism information is detected based on whether the average value of the variation amount exceeds a previously determined threshold.

20. A non-transitory computer readable medium having embodied thereon computer readable instructions which, when executed by a computer, causes the computer to realize a method of determining a reliability of organism information of a subject utilizing digital data of an organism signal outputted by organism information detecting means of an organism information detecting apparatus that detects the organism information of the subject by being brought into contact with the subject, the method comprising:
   reading the digital data;
   calculating an average value of a variation amount per time of the digital data;
   determining the motion state of the subject when the organism information is detected based on whether the average value of the variation amount exceeds a previously determined threshold; and
   determining a reliability degree of the organism information based on whether the motion state is a previously determined motion state.

* * * * *